United States Patent [19]

Mikkelsen et al.

[11] Plant 4,781

[45] Oct. 27, 1981

[54] BEGONIA PLANT

[75] Inventors: James C. Mikkelsen; Cornelis P. Van den Berg, both of Ashtabula, Ohio

[73] Assignee: Mikkelsens Inc., Ashtabula, Ohio

[21] Appl. No.: 133,900

[22] Filed: Mar. 25, 1980

[51] Int. Cl.[3] ..... A01H 5/00

[52] U.S. Cl. ..... Plt./68

[58] Field of Search ..... Plt./68

*Primary Examiner*—Robert E. Bagwill

*Attorney, Agent, or Firm*—Schwartz, Jeffery, Schwaab, Mack, Blumenthal & Koch

[57] ABSTRACT

A begonia plant referred to by the cultivar name Fresco having large semi-double to double, deep orange-red flowers; heavy infusion of red pigmentation in the foliage; pleasant contrast of flower and foliage color; year round flowering with proper environmental conditions, and a vigorous growth habit.

1 Drawing Figure

The present invention relates to a new and distinctive cultivar of begonia plant, botanically known as *Begonia x hiemalis Fotsch,* and hereinafter referred to by the cultivar name Fresco.

The new cultivar was discovered by us as a mutation of Renaissance, an unpatented cultivar, with the new cultivar being observed in a group of flowering stock plants of the parent. Asexual reproduction by leaf cuttings taken in Ashtabula, Ohio has confirmed that Fresco propagates true to type through successive propagations.

The following characteristics distinguish Fresco from both its parent and other begonias commercially known and used in the floriculture industry:

1. The foliage is infused with red pigments, causing young leaves to be dark brown-red and mature leaves dark green-red, comparable with the foliage of Krefeld Orange, disclosed in U.S. Plant Pat. No. 3,753.
2. Flower is large, semi-double to double, deep orange-red, similar to the flower of the parent cultivar Renaissance.
3. Stems, petioles and peduncles are dark red.
4. Flower color and foliage color combined form a striking contrast.
5. Can be flowered year round by proper manipulation of the environment.
6. Number of flowers per peduncle, floriferousness and flowering date are similar to those characteristics of Renaissance.
7. Fresco is a vigorous grower, and therefore especially well suited for 13 cm. and larger pots; can also satisfactorily be grown in a 20 cm. or 25 cm. hanging basket.
8. Application of the growth regulator Cycocel will decrease the length of the peduncles and the overall height of the plant.
9. Propagation by means of leaf cuttings is similar to that of Renaissance.

The accompanying colored photograph illustrates the new cultivar, with the colors being as true as it is reasonably possible to obtain in a colored reproduction of this type.

The following is a detailed description of the new begonia cultivar based on plants produced under commercial practices in greenhouses of Mikkelsens Inc. in Ashtabula, Ohio. Color references are made to the Royal Horticultural Society Colour Chart except where general color terms of ordinary dictionary significance are used.

Parentage: Mutation of *Begonia x hiemalis Fotsch* cv. Renaissance.

Propagation:

(A) *Type cutting.*—Leaf cuttings.

(B) *Time to root.*—3–4 weeks at temperature of the growing medium of 21° C.

(C) *Rooting habit.*—Fine, fibrous, abundant.

(D) *Time for shoot development.*—9 weeks in summer to 13 weeks in winter, to obtain shoots of approximately 4–5 cm. in length.

Plant description:

(A) *Form.*—Generally upright, with good vigor for self-support. Growing and scheduling practices and application of Cycocel can result in a medium size plant in a 13 cm. pot or a relatively larger plant in a 20 cm. pot.

(B) *Habit of growth.*—Fast grower for this type of begonia; generally, vegetative shoots are formed at the basal nodes and flowers at the higher nodes.

(C) *Foliage.*—Leaves simple, alternate, borne on strong petioles, 5 mm. in diameter when full grown. (1) Size: widely varying depending on position on the plant and the environmental conditions; up to 15×20 cm. when full grown. (2) Shape: ovate. (3) Texture: leathery, glabrous. (4) Margin: lobed, with strongly acuminate incisions and secondary serration. (5) Color: young foliage top side, yellow green 146A, heavily infused with red, under side green, heavily infused with red. Mature foliage top side, green 137A, heavily infused with red, under side green, heavily infused with red. The amount of red pigments in the leaves, and thus the foliage color, depends on growing conditions, the age of the leaf, and the position of the leaf on the plant. (6) Veination: 7–8 main veins.

Flowering description:

(A) *Flower habits.*—Flowers in cymes, generally consisting of two branches after the first flower, with each of these branches generally branching again.

(B) *Natural flowering season.*—Throughout the year, although plant will flower in an earlier stage of development under short day conditions.

(C) *Flower bud description.*—Round across, U-shaped in side view, up to 20 mm. before opening; tepals appear to be serrated around the margin, which in later development changes to a wavy pattern of the unfolded tepals; color red 45A for immature buds to red 43A just before opening.

(D) *Flowers borne.*—On strong, upright peduncles, red 46A, main peduncle 5 mm. in diameter.

(E) *Quantity.*—Average of 3–5 flowers per peduncle, opening up in sequence.

(F) *Flowers on the same axis.*—Can vary from semi-double to extremely double.

(G) *Tepals.*—(1) Shape: nearly round, with margins wavy. (2) Color: top side in winter when opening, red 44 A-B, fading to red 44C; under side red 41A to red 44C. (3) Number of tepals: 8 to 60, depending on doubleness of flower.(4) Size of tepals: 30 mm. in diameter when full grown. (5) Flower size: 60 mm. in diameter when fully opened.

(H) *Reproductive organs.*—(1) Stamens: up to 80 in number, depending on doubleness. (a) Anther shape: spoon-shaped, color red 43A. (b) Pollen: not released. (2) Pistils: none observed to date.

Disease resistance: Resistance to powdery mildew is the same as that of the parent cultivar Renaissance.

We claim:

1. A new and distinct cultivar of begonia plant referred to by the cultivar name Fresco, as described and illustrated, and particularly characterized by its large semi-double to double, deep orange-red flowers; heavy infusion of red pigmentation in the foilage; pleasant contrast of flower and foliage color; year round flowering with proper environmental conditions, and by its vigorous growth habit.

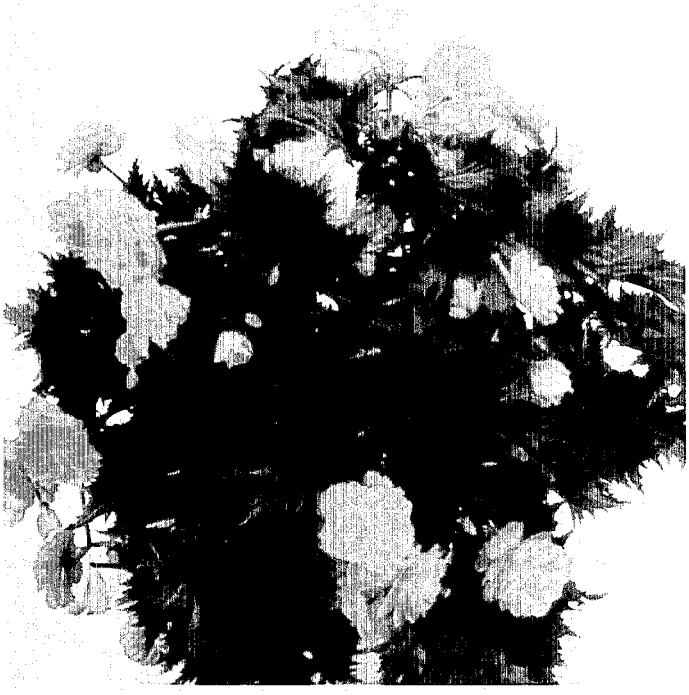

* * * * *